United States Patent [19]

Hagerstrom

[11] Plant 4,413

[45] May 15, 1979

[54] STRAWBERRY PLANT - CRIMSON KING VARIETY

[75] Inventor: Marion Hagerstrom, Monticello, Minn.

[73] Assignee: Stark Brothers Nurseries & Orchards Company, Louisiana, Mo.

[21] Appl. No.: 873,560

[22] Filed: Jan. 30, 1978

[51] Int. Cl.[2] ..... A01H 5/03

[52] U.S. Cl. ..... Plt./48

[58] Field of Search ..... Plt./48

*Primary Examiner*—Robert E. Bagwill

*Attorney, Agent, or Firm*—Burns, Doane, Swecker & Mathis

[57] ABSTRACT

The new and distinct improved variety of strawberry plant resulted from crossing the Trumpeter variety (unpatented) with the Red Giant variety (U.S. Pat. No. 2,884). The plant bears a general resemblance to the Red Giant variety, but forms fruit which ripens a week to ten days earlier which is of better flavor and remains of a uniform large size throughout the picking season.

1 Drawing Figure

SUMMARY OF THE INVENTION

The original plant was selected from a family of seedlings resulting from a cross made in 1972 at Monticello (Wright County), Minn. between the Trumpeter variety (unpatented) and the Red Giant variety (U.S. Plant Pat. No. 2,884). The Red Giant variety was available commercially from the Stark Bro's Nurseries and Orchards Co. under the registered trademark "Stark".

As a result of this breeding, I have produced a new and distinct improved variety of strawberry plant which is distinguished from its parents, as well as from all other varieties of which I am aware.

The present variety, which has been designated the Crimson King variety, bears a general resemblance to the Red Giant variety (U.S. Plant Pat. No. 2,884), but forms fruit which ripens a week to 10 days earlier which is of better flavor and remains of a uniform large size throughout the picking season. The fruit color of the Crimson King variety is substantially identical to that of the Red Giant variety (U.S. Plant Pat. No. 2,884).

Asexual reproduction of my improved strawberry variety by runners as performed by me at Monticello, Minn. beginning in 1975 shows that the foregoing characteristics and distinctions come true to form, and are established and transmitted through succeeding propagations.

BRIEF DESCRIPTION OF THE DRAWINGS

The accompanying drawing shows typical specimens of the fruit and foliage of my new variety, with the fruit specimens shown in various stages of development, all as depicted in color as nearly true as it is reasonably possible to make the same in a color illustration of this character.

DETAILED DESCRIPTION

The following is a detailed description of the new variety's characteristics as observed from plants growing at Louisiana, Mo. Color terminology is in accordance with Nickerson's Color Fan, published by Munsell Color Company, Inc., of Baltimore, Md., except where general color terms are to be accorded their usual dictionary significance.

Dates of first and last pickings during 1977: May 19 and June 1 respectively.

Plant:

*Growth.*—Vigorous.

*Root.*—Vigorous.

*Crown.*—Simple; medium size.

*Leaves.*—Many; large size. Petiole — medium long and stout; petiole of central leaflet exceeds that of lateral by one-half longer. Color — upper surface — dark green. Lower surface — medium light green. Pubescence — scant. Groove — shallow. Serrations — irregular, broadly ovated. Ciliate on margin and having green apex; serrations of both central and lateral leaflets extend over upper $\frac{3}{4}$ of margin.

*Leaflets.*—Upper surface — dull smooth flat; color dark green. Lower surface — medium light green. Pubescence — scant.

*Runners.*—Appear during fruiting; numerous; stocky.

*Flower stems.*—Medium short; inflorescence protected by foliage.

Bloom: Medium early.

*Date of first bloom.*—April 29.

*Date of full bloom.*—May 7.

*Flowers*—Many; perfect. Breadth: Primary — $1\frac{1}{4}$ inches. Secondary — filaments of stamens — short. Pollen — abundant.

Fruiting stems:

*Medium stout.*—Upright.

*Radical.*—Shorter than main truss.

*Branches of truss.*—Few.

Soil where grown: Loamy; fairly well drained.

Culture: Mulched with straw; sprayed with benomyl fungicide and diazon insecticide; matted row thinned.

Fruit:

*Condition when described.*—Prime; May 25.

*Size.*—Uniform; large; constant throughout season. Average length — $1\frac{1}{2}$ inches. Average breadth — $1\frac{5}{8}$ inches. Average thickness — $1\frac{3}{8}$ inches.

*Form.*—Uniform; regular; obtuse-conical; apex rounded. Shallow groove on one side of largest specimens.

*Stems.*—Medium stout; medium long; main truss stout.

*Calyx.*—Even with surface. Medium free; medium large size; green after picking. Upper surface: Color — medium dark green. Pubescence — scant. Lower surface: Color — light green; pubescence — very scant.

*Surface.*—Glossy. Color — vivid carmine red (Strong Red Hue 5R 4/12).

*Seeds.*—Color — light straw yellow. Markings — none.

*Core.*—Most fruits are solid, very few with small hollow area. Color — light pinkish red (Vivid Red, Hue 5R 5/13) surrounded with white. As the fruit reaches full soft maturity, the white gradually turns to vivid red.

*Flesh.*—Juicy. Color — vivid bright red (Vivid Red, Hue 5R 5/13).

*Flavor.*—Very rich subacid.

*Quality.*—Best. Shipping Quality — good.

*Use.*—Market; dessert.

I claim:

1. A new and distinct variety of strawberry plant, substantially as herein shown and described, characterized particularly as to novelty by the unique combination of a general resemblance to the Red Giant variety (U.S. Plant Pat. No. 2,884), but forming fruit which ripens a week to 10 days earlier which is of better flavor and remains of a uniform large size throughout the picking season.

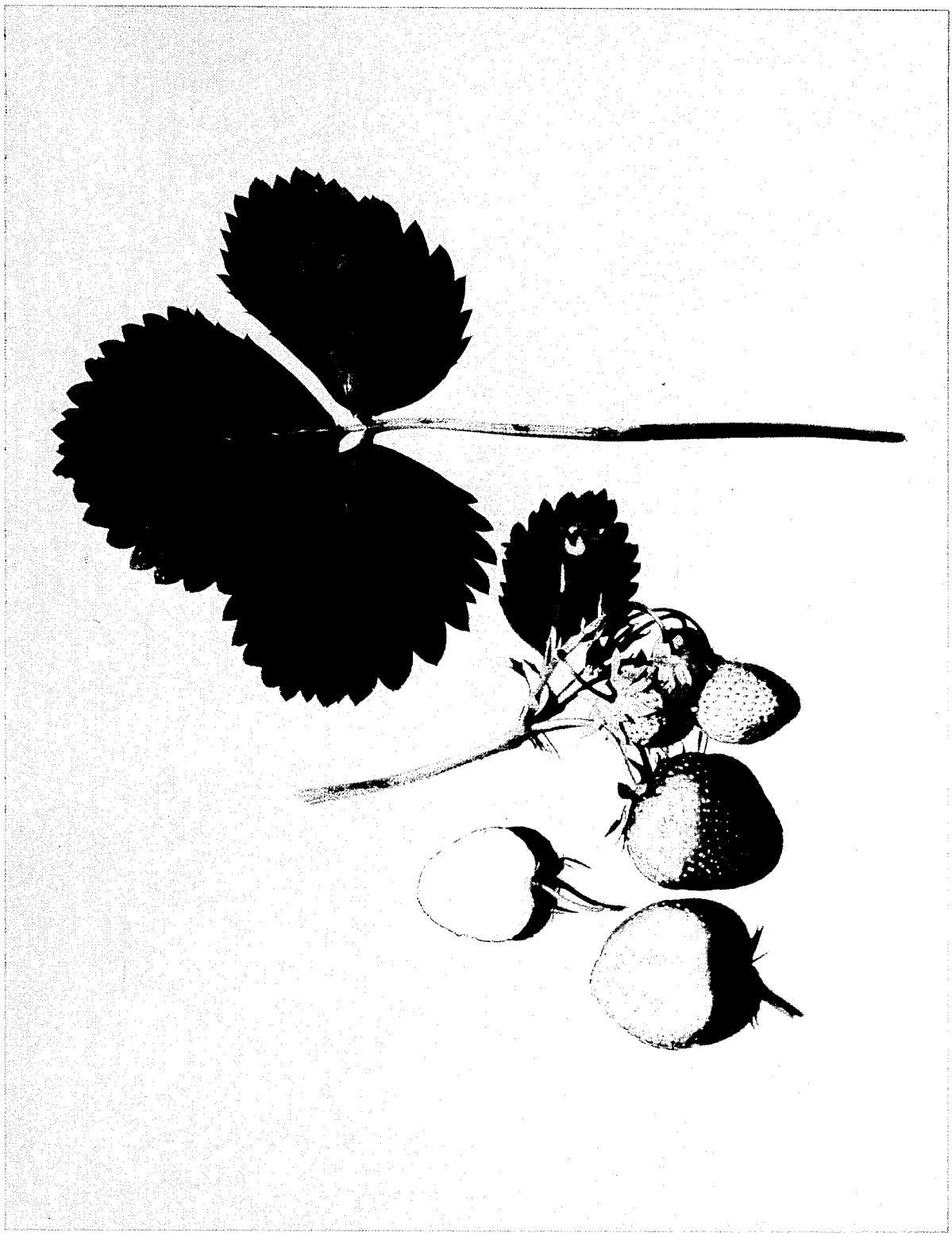

* * * * *